United States Patent [19]
Yoshida

[11] Patent Number: 4,486,776
[45] Date of Patent: Dec. 4, 1984

[54] INSPECTION APPARATUS
[75] Inventor: Hajime Yoshida, Tokyo, Japan
[73] Assignee: Hajime Industries, Ltd., Japan
[21] Appl. No.: 386,708
[22] Filed: Jun. 9, 1982
[30] Foreign Application Priority Data
Jun. 19, 1981 [JP] Japan .................. 56-95759
[51] Int. Cl.³ .................. H04N 7/18; G01P 3/40; G06K 9/32
[52] U.S. Cl. ...................... 358/106; 356/23
[58] Field of Search ............ 358/101, 106, 107; 356/23

[56] References Cited
U.S. PATENT DOCUMENTS
4,305,658 12/1981 Yoshida ................. 358/106
4,318,081 3/1982 Yoshida ................. 358/107
4,380,026 4/1983 Kubota .................. 358/101

Primary Examiner—Howard W. Britton

[57] ABSTRACT

Systems that judge the good or bad of moving objects to be inspected by processing image signals from a video camera which picks up the objects at an inspection circuit, are disclosed whereas each time the moving objects to be inspected arrive at the position to be inspected, a position detection signal is generated from a position detection system. This position detection signal drives the light source to irradiate light for a short time period onto the object to be inspected when it arrives at the inspection position and then such irradiated inspected object is picked up by the video camera as a static image. In this case, the image signal and position detection signal are both applied to a signal process and generation circuit so that this circuit generates a control signal with the voltage corresponding to the level of the image signal of the first field and also an enable signal at high level during the second field period of the image signal, and then the image signal, control signal as well as enable signal are all fed to the inspection circuit to drive the same during the period in which the enable signal is at high level, whereby the inspection system carries out the inspection to judge the good or bad of the inspected objects based on the image signal of the second field.

5 Claims, 18 Drawing Figures

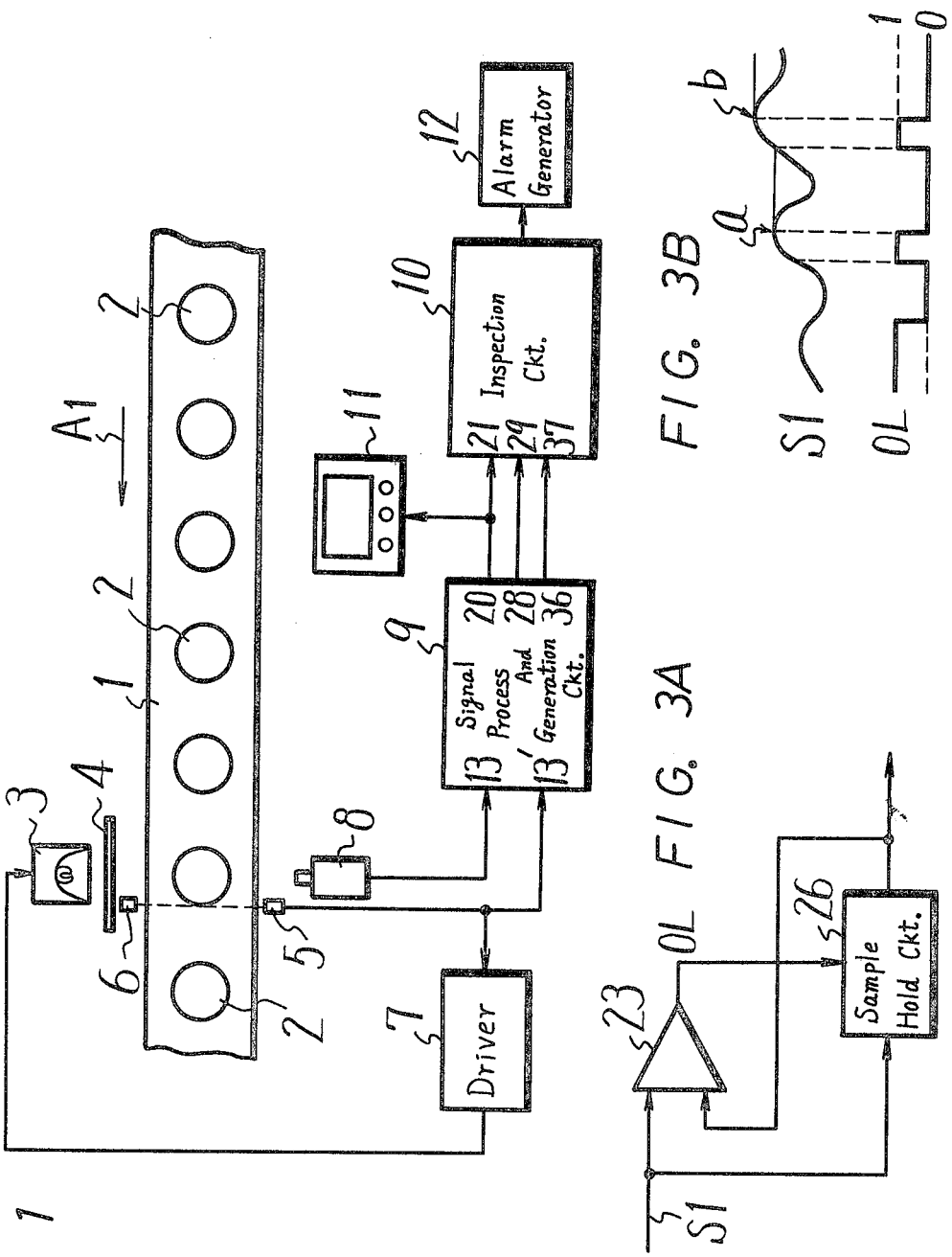

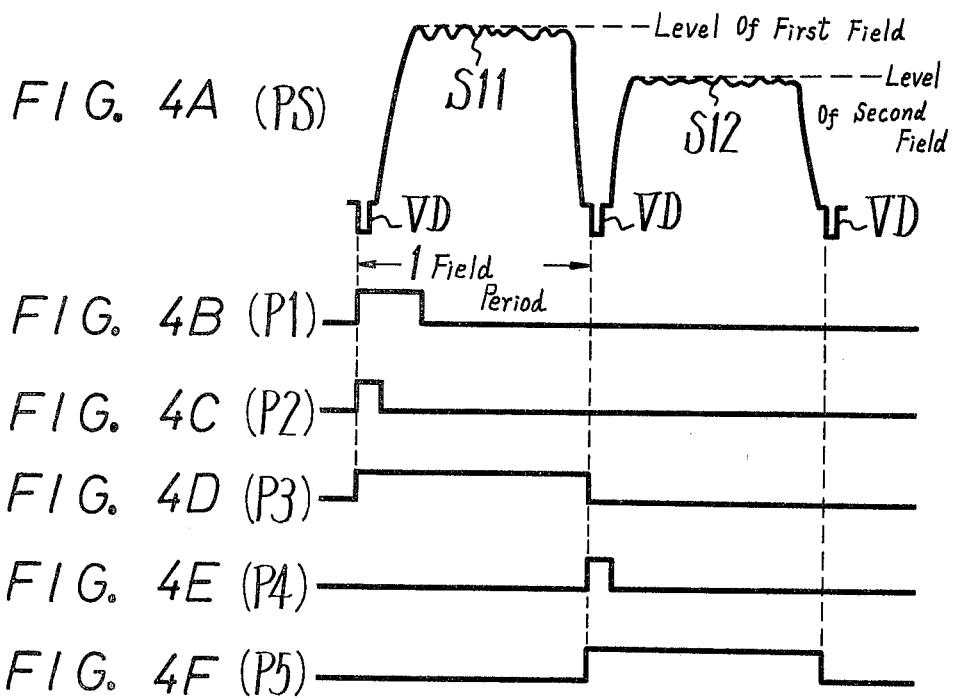
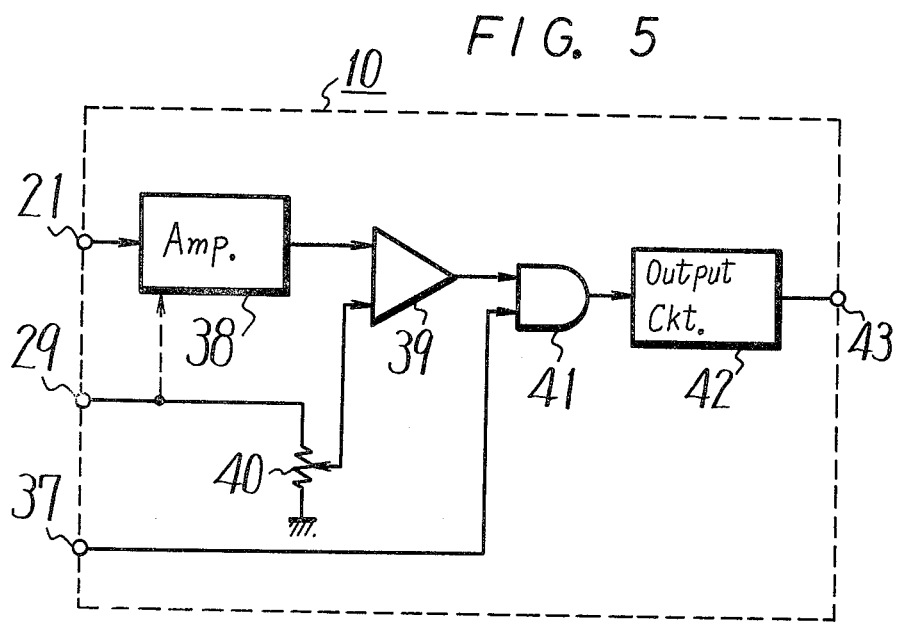

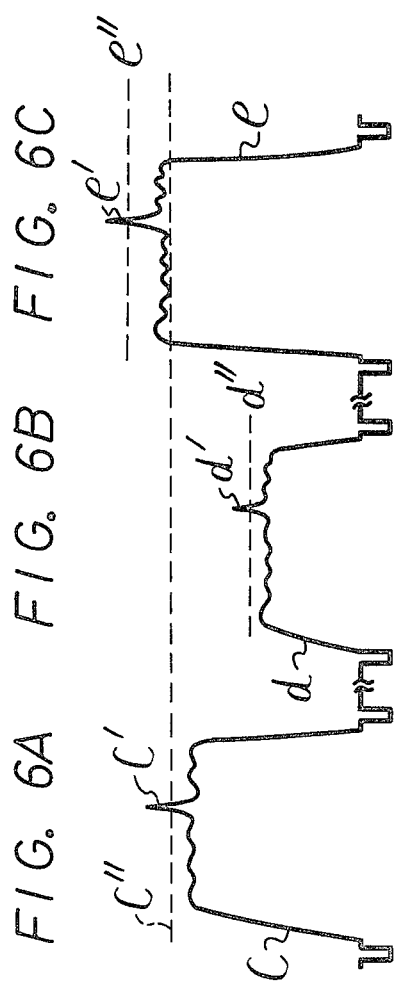
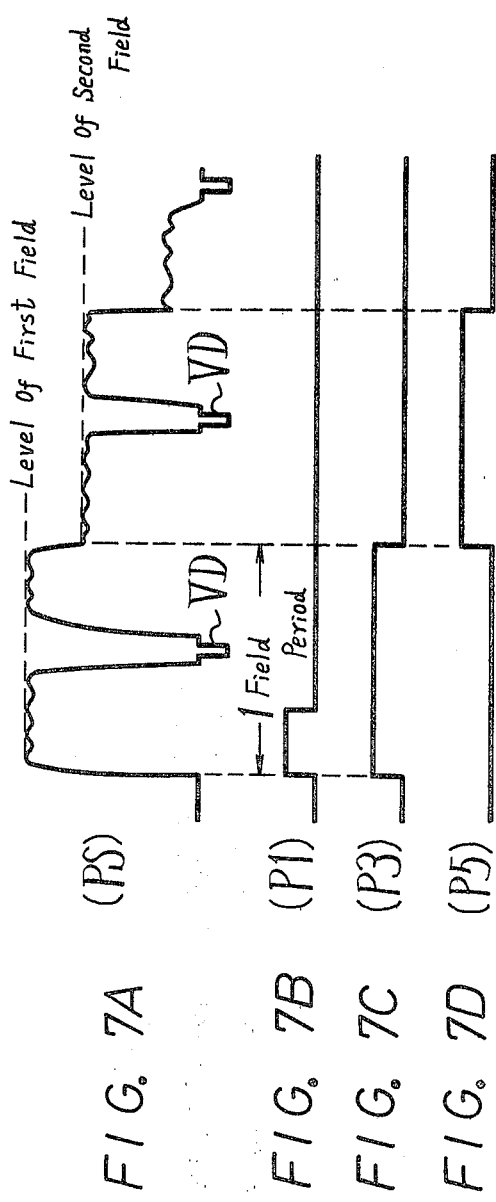

INSPECTION APPARATUS

BACKGROUND OF THE INVENTION

1. Field of the Invention

The present invention is generally related to inspection systems for objects, and more particularly to such inspection systems that automatically inspect moving products or the like by using video cameras or the like.

2. Description of the Prior Art

During the recent years, the inspection of components or products or the like has advanced with a trend to provide labour savings at the inspection processes, or further to the "no man" operations, by changes from the human dependent visual inspection to automatic inspection by image signal processing of the utilized photo sensors or video cameras or the like. At present, where various production processes for such products are increasingly commenced with high speeds, the inspection processes are required to cope with these increased high speeds.

Attempts have been proposed to inspect such products that flow with high speed on conveyers or the like, by using video cameras as an example. At such systems, stroboscopes or the like are used as the lighting source to irradiate on the products for a short time period, so that the product may be caught as a static image on the photo sensing or target screen of the video camera, and then by processing the image signal delivered from the video camera, conducts the product inspection.

In the case of inspecting products or the like by video cameras, it is normally necessary to throw light onto the products. As for such lighting methods, there are various methods of irradiation, such as reflection lighting or through lighting and others, but in order to accurately inspect such products by video cameras or the like, it is an important condition that the intensity of the light irradiating on the products are constant.

Even when the light intensity for lighting from the light source is constant, an accurate inspection cannot be expected if the light intensity that enters the video camera is not constant after reflection from the product to be inspected or through passing the product. As an example, in the case of reflection lighting use, although the light intensity from the light source is constant, the reflection light intensity varies depending upon the base colour of the object under irradiation. On the other hand, in the case of a through lighting method, although the intensity from the light source is constant, for instance, such as in the case of glass bottle inspection (bottle bottom, bottle body), the intensity of the light passing there through will vary by the colour irregularities of the coloured bottles.

At the conventional systems, there is no compensation or counter measures to deal with variations in the light intensities that are picked up by the video camera. Accordingly in such above cases, an accurate inspection cannot be anticipated.

OBJECTS AND SUMMARY OF THE INVENTION

Accordingly, it is a main objective of the present invention to provide a novel inspection system which will accurately and positively be able to inspect objects although the light intensity picked by the video camera from the objects may vary depending upon each object.

According to an aspect of the present invention there is provided an object inspection system which comprises:

(a) position detecting means for detecting arrival of an object to be inspected at an inspection position and for generating a position detection signal at every time when said object arrives at the inspection position;

(b) irradiation means for irradiating said object which arrives at the inspection position with light in a short period of time in response to said position detection signal;

(c) image sensing means for picking up said object which arrives at the inspection position and irradiated with the light as a static image and for generating an image signal;

(d) inspection means for processing the image signal from said image sensing means to inspect whether said object is good or bad; and (e) means supplied with both of the image signal and position detection signal for generating a control signal with a voltage corresponding to a level of an image signal of a first image period in said image signal and also an enable signal which is in a high level during a period of an image signal of a second image period in said image signal, said inspection means being supplied with said image signal, control signal and enable signal whereby said inspection means is driven during a period where said enable signal is in a high level to conduct said inspection of said object based upon said image signal of the second image period.

The other objects, features and advantages of the present invention will become apparent from the following description taken in conjunction with the accompanying drawings.

BRIEF DESCRIPTION OF THE DRAWINGS

FIG. 1 is a systematic block diagram showing an example of the inspection system for objects by the present invention;

FIGS. 3A and 3B are schematic and waveform diagrams used to explain the function of a part of the example shown in FIG. 2;

FIGS. 4A, 4B, 4C, 4D, 4E and 4F are waveform diagrams used to explain the function of a part of the example shown in FIG. 2;

FIG. 5 is the connection diagram of an example of the inspection circuit shown on FIG. 1;

FIGS. 6A, 6B and 6C are waveform diagrams to explain the functions thereof; and

FIGS. 7A, 7B, 7C and 7D are waveform diagrams used to explain the operation of another example according to the present invention.

DESCRIPTION OF THE PREFERRED EMBODIMENTS

Figure 2:
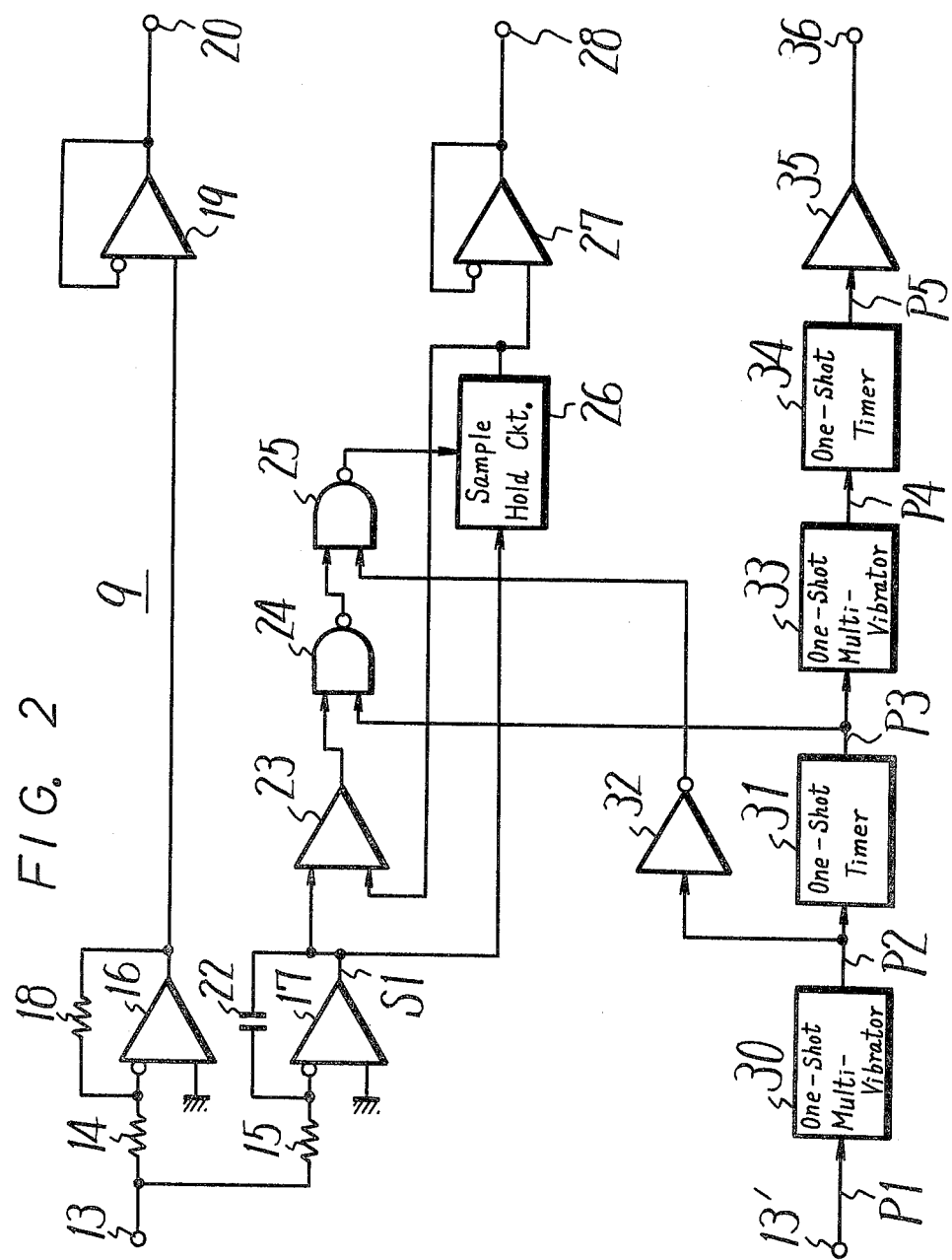
FIG. 2 is a connection diagram of an example of the main part of such system.

One example of the inspection system for objects under the present invention will be explained in reference with the attached drawings hereunder.

FIG. 1 illustrates a systematic and schematic block diagram of an example of the total inspection system of the invention that is used to inspect objects by photo electric conversion means such as video cameras or the like. On the drawing, 1 is a conveyer such as a belt conveyer, on which objects 2 to be inspected such as glass bottles flow at high speed in the direction indicated by an arrow A1. 3 designates a light source such as a stroboscope or the like, which irradiates upon such bottles 2 as an example, whereas the light beams from light source 3 irradiate the bottle 2 when it arrives at the inspection position after passing through a light diffuser plate 4, by way of example. 5 and 6 are a light receiver and a light emitter as an example, which construe a position detection system which detects that the bottle 2 has arrived at the inspection position. When bottle 2 arrives at the inspection position, light receiver 5 generates a position detection signal and delivers the same to a drive circuit 7 for the stroboscope 3. Therefore, every time the bottle 2 arrives at the inspection position, the stroboscope 3 is lighted by the drive circuit 7 to generate a flash. When bottle 2 arrives at the inspection position, and the stroboscope 3 is lighted to irradiate on the bottle 2 for a short time period, the video camera 8 as a photo electric conversion means catches or picks up the bottle 2 as a static image on its target screen. The image signal from video camera 8 is passed through a signal process and generation circuit 9 and is delivered to an inspection circuit 10, whereat the image signal is processed to inspect the existence or not of defects such as flaws or dirty on the inspected object 2 such as bottles or the like. Further, the image signal from the signal process and generation circuit 9 may be delivered to a television monitor 11 so that the bottle 2 may be visually watched. In FIG. 1, 12 is an alarm generator that generates an alarm such as sound generating or lamp lightening when the bottle 2 is abnormal, for instance when there are flaws or dirtiness on bottle 2, by receiving the output signal that is generated at the inspection circuit 10.

Next, in reference with FIG. 2, the details of an example of the signal process and generation circuit 9, which is a main construction element of the present invention will be explained. On FIG. 2, 13 is an input terminal of the signal process and generating circuit 9, and the image signal from the video camera 8 is delivered to this input terminal 13. The image signal that was input to this terminal 13 is respectively delivered through resistors 14 and 15 to operational amplifiers 16 and 17. One operational amplifier 16 slightly amplifies the delivered image signal by the existence of resistors 14 and 18. This is owing to the fact that, at the present invention, as later described, by the flash generated from the stroboscope 3, the bottle 2 which is the inspected object is picked up by the video camera 8 as a static image, which produces an image signal whose one frame consists of, for example, first and second field signals, and then the image signal during the first field is used to measure the intensity or amount of the light from bottle 2 at the inspected time, and thereafter the image signal during the second field by the residual image on the photo sensing area or target screen of video camera 8 is used to actually inspect the bottle 2, whereas the level of the image signal during the second field as obtained from the residual image is lower than that of the image signal during the first field. This ratio of level drop varies depending upon kinds of the electronic pick-up tube that is used in the video camera 8, but for instance, in the case of a Vidicon Tube, the level of the image signal during the second field is at about 70 percents of that of the image signal of the first field. Therefore, operational amplifier 16 is used to recover the level of the image signal of the second field. In the case where the Vidicon Tube is used as an example, the operational amplifier 16 amplifies the image signal to about 1.4 times. The image signal from operational amplifier 16 is passed through buffer 19 and is delivered to output terminal 20 of the signal process and generation circuit 9. This output terminal 20 is connected to input terminal 21 of the inspection circuit 10 as hereafter described.

The other operational amplifier 17 construes an integrator with resistor 15 and capacitor 22 to smooth out the image signal applied thereto. The smoothed image signal S1 by operational amplifier 17 is passed through comparator 23, NAND gates 24, 25 as well as sample hold circuit 26 to form a control signal (later described) that controls the function of the inspection circuit 10. This control signal is delivered through buffer 27 to output terminal 28 of the signal process and generation circuit 9. This output terminal 28 is connected to input terminal 29 for the control signal at the inspection circuit 10.

Now, the generating operation of the aforementioned control signal will be explained in reference with FIGS. 3A and 3B. It is noted that while NAND gates 24, 25 are omitted in FIG. 3A, but since two NAND gates 24, 25 are removed, the control logic for the sample hold circuit 26 in case of FIG. 3A is the same as that of the case of FIG. 2. The control logic for sample hold circuit 26 from comparator 23 is so assumed that when it is "1" the sample hold circuit 26 becomes the sample mode while when it is "0" the sample hold circuit 26 becomes the hold mode. The smoothed image signal S1 from operational amplifier 17 is delivered to one of the input terminals of comparator 23 and the output signal from the sample hold circuit 26 is delivered to the other input terminal of comparator 23. At this time, if the image signal S1 is larger than the output signal of the sample hold circuit 26, the output logic OL of the comparator 23 that is delivered to the sample hold circuit 26 becomes "1", which causes the sample hold circuit 26 to be at the sample mode, but when the image signal S1 that is delivered to comparator 23 is smaller than the output from sample hold circuit 26, the output logic OL from the comparator 23 becomes "0" which causes the sample hold circuit 26 to be at hold mode, so that the previous analog input image signal S1 is held within the sample hold circuit 26 as it is. Next, when the input image signal S1 supplied to one of the input terminals of comparator 23 is larger than the output from the image signal S1 from the sample hold circuit 26 which is delivered to the other input terminal of comparator 23, the sample hold circuit 26 starts to sample image signal S1 again. In other words, as shown on FIG. 3B, the sample hold circuit 26 enters the hold mode at the first peak level a of the input image signal S1, and then enters the sample mode at a higher level than the level a of image signal S1 and then enters the hold mode again at a higher peak level b than the peak level a of the image signal S1. Therefore this sample hold circuit 26 has a function of peak hold. In other words, the image signal that was delivered to input terminal 13 is smoothened at operational amplifier 17, and the peak level of the smoothened image signal S1 is detected by comparator 23 and sample hold circuit 26 and then held in the sample hold circuit 26. This held signal is delivered to the input terminal 29 of the inspection circuit 10 as the control signal through buffer 27 and output terminal 28.

As the next step, the functions of NAND gates 24 and 25 will be explained in reference with the waveforms shown on FIGS. 4A through 4F. FIG. 4A shows the two consecutive fields of image signal PS from the video camera 8. Since an image signal S12 of the second field can be obtained by utilizing the residual image phenomenon as previously described, the level thereof is lower than that of an image signal S11 of the first field. Note that VD on the same drawing shows the vertical synchronizing signal. FIG. 4B shows the position detection signal P1 which is generated when the bottle 2 to be inspected arrives at the inspection position by the light receiver 5 of the position detection system. In this example, the vertical synchronizing signal VD synchronizes with position detection signal P1. This signal P1 is delivered to one-shot multi-vibrator 30 through the input terminal 13′ of the signal process and generation circuit 9 shown on FIG. 2. Then, this one-shot multivibrator 30 generates a trigger signal P2 as shown on FIG. 4C and delivers the same to one-shot timer 31. Then, one-shot timer 31 generates a strobe signal P3 as shown on FIG. 4D. This strobe signal P3 is at high level during the first field period of image signal S11 as shown in FIG. 4D. This strobe signal P3 is delivered to one of the input terminals of NAND gate 24 the other input terminal of which is supplied with the output from comparator 23 as set forth above, whereby the peak hold function of the aforementioned sample hold circuit 26 is controlled. In other words, only when the output strobe signal P3 from the one-shot timer 31 is at high level, the NAND gate 24 makes the sample hold circuit 26 enter the peak hold function. That is to say that, during the high level period of strobe signal P3, namely the field period of the first field image signal S11, the sample hold circuit 26 holds the peak value of the input image signal S1, and after the level of the signal P3 becomes the low level, the sample hold circuit 26 continues to hold the ultimately held value. The output signal P2 of one-shot multi-vibrator 30 is also delivered through NAND buffer 32 to one of the input terminals of NAND gate 25 as a reversed logic signal. To the other input terminal of this NAND gate 25, the output signal of NAND gate 24 is delivered. The output signal of NAND gate 25 is delivered as the aforementioned control logic signal to sample hold circuit 26, so that when the bottle 2 arrives at the position to be inspected and the light receiver 5 generates the position detection signal P1, the peak value held till then at the sample hold circuit 26 is cleared up and it becomes the mode to perform a new peak hold function. That is, the output of NAND gate 25 at this time serves to achieve a so-called reset for the sample hold circuit 26.

The output strobe signal P3 from one-shot timer 31 is also delivered to one-shot multi-vibrator 33. This one-shot multi-vibrator 33 generates a pulse signal P4 of a short width as shown on FIG. 3E in synchronization with the trailing edge of strobe signal P3. This pulse signal P4 is delivered to one-shot timer 34 by which signal P5 that is at high level during the field period of the second field image signal S12, as shown on FIG. 4F is obtained. This signal P5 is delivered to input terminal 37 of the inspection circuit 10 through buffer 35 and output terminal 36 of the signal process and generation circuit 9. This signal P5 is used as the enable signal to make the inspection circuit 10 conduct the inspection function. In other words, while the signal P5 is at high level, that is to say that, during the field period of the second field image signal S12, the inspection circuit 10 inspects the image signal S12 as described later.

As the next step, the operation of inspection circuit 10 will be explained in reference with FIG. 5 which shows an example of the inspection circuit 10 as well as FIG. 6 which shows the enable signal and image signal of the inspected object such as bottle 2 that are delivered to the inspection circuit 10 from the video camera 8 and the position detection system through the signal process and generation circuit 9. The image signal from the output terminal 20 of the signal process and generation circuit 9 is delivered to one of the input terminals of comparator 39 after passing the input terminal 21 of the inspection circuit 10 and its image signal amplifier 38. On the other hand, the control signal from output terminal 28 of circuit 9 is delivered to the other input terminal of comparator 39 after passing input terminal 29 of circuit 10 and its potentiometer 40. Now, it be assumed that the image signal that is delivered to one input terminal of comparator 39 is such as shown on FIG. 6A at c and it contains an abnormal portion or level c′ which corresponds to a defect such as a flaw on bottle 2 of the inspected object as shown in FIG. 6A. Since the inspection circuit 10 is formed to detect such abnormal portion or level c′, if the threshold level of the comparator 39 is set by potentiometer 40 based on the control signal to be at such level as c″ which is lower than the peak value of level c′ as shown on FIG. 6A, the abnormal level c′ can be detected. However, if the intensity or amount of the incident light from the inspected object 2 to the video camera 8 varies by some cause and the brightness of the image signal from the video camera 8 varies with the result that the image signal becomes those d and e as shown on FIGS. 6B and 6C whose levels greatly differ to that of the image signal level c, the abnormal levels d′ and e′ of image signals d and e cannot be detected with the threshold value c″ in relation to image signal c. In order to detect the abnormal levels d′ and e′ on image signals d and e, as shown on FIGS. 6B and 6C, the threshold values for the image signals d and e will have to be arranged as d″ and e″ respectively. However, with the present invention, since the control signal delivered to the other input terminal of comparator 39 is such one that, as aforementioned, it is formed at circuit 9 as based on the image signal of the first field in response to each inspected object from the video camera 8, as shown on FIGS. 6B and 6C, even though the levels of the image signals are varied, the control signal has an adjusted voltage in response to each of the image signals. Therefore, if potentiometer 40 is set once to determine the threshold value of comparator 39 as, for example, c″ for the image signal c on FIG. 6A, although the image signals may vary as d and e on FIGS. 6B and 6C, the threshold values will automatically change to d″ and e″ to make such inspections possible.

Comparator 39 generates an output when there is an abnormality in the image signal. While this output is delivered to one input terminal of AND gate 41, the other input terminal thereof receives delivery of the enable signal P5, which is at high level during the field period of the second field image signal, from output terminal 36 of circuit 9 through input terminal 37. Therefore, the output of AND gate 41 corresponds to the inspection results of the image signal of the second field. This output from AND gate 41 is delivered to an alarm generation system 12, as shown on FIG. 1 as an example to output an alarm after passing output circuit 42 which construes a timer, buffer, etc. and output terminal 43.

When there are no abnormalities as above described on the image signals, the comparator 39 gives no output signal so that there will be no alarm generated. In other words, whenever there are no abnormalities in the image signals, the alarm circuit does not generate any output, so that the inspected objects are judged as good products.

Further, when the inspected object is a bad product whereas the image signal contains an abnormality, it is needless to say that the signal that is generated by the output circuit 42 of the inspection circuit 10, although not shown in the drawings, may be used to reject the bad products from the conveyer 1 by driving the bad product rejection system that is located after the inspection position of the inspected objects 2 on the conveyer 1.

In the above described example of the present invention, as shown on FIG. 4, the vertical synchronizing signal VD of the image signal PS is sychronized with signal P1 which is generated when the inspected object 2 arrives at the position to be inspected, but it need not be confined as such. For instance, as shown on FIG. 7, even when the vertical synchronizing signal VD of the image signal PS does not synchronize with signal P1, the signal P3 from one shot timer 31, as shown on FIG. 7, is at high level during the period corresponding to that of the first field image signal in the same manner to the signal shown on FIG. 4D, and the aforementioned control signal is provided from the image signal of the first field, and further, the signal P5 from the one-shot timer 34 is, as shown on FIG. 7D, in the same manner to the signal shown at FIG. 4F, is at high level during the period corresponding to that of the second field image signal, so that the second field image signal may be used to inspect the objects to be inspected.

In the above example of the invention, the video camera produces such the image signal whose one frame consists of two fields, but it may be apparent that this invention can employ such a video camera which produces an image signal whose one frame consists of one field or the like.

Further, while at the above described example of the present invention, the control signal is used as the threshold value setting signal for comparator 39 after passing potentiometer 40, it is obvious that the same effects to the above example may be obtained by fixing the threshold value of comparator 39 at constant, and by controlling the amplification degree of the prior stage amplifier 38 with the control signal (refer to the dotted line in FIG. 5) so that a steady level image signal is always obtained.

The above description is given on one preferred embodiment of the present invention, but it will be apparent that many modifications and variations could be effected by one skilled in the art without departing from the spirits or scope of the novel concepts of the invention. Therefore, the spirits or scope of the invention should be determined by the appended claims only.

I claim as my invention:
1. An object inspection system, comprising:
    (a) position detecting means for detecting arrival of an object to be inspected at an inspection position and for generating a position detection signal at every time when said object arrives at the inspection position;
    (b) irradiation means for irradiating said object which arrives at the inspection position with light in a short period of time in response to said position detection signal;
    (c) image sensing means for picking up said object which arrives at the inspection position and irradiated with the light as a static image and for generating an image signal;
    (d) inspection means for processing the image signal from said image sensing means to inspect whether said object is good or bad; and
    (e) means supplied with both of the image signal and position detection signal for generating a control signal with a voltage corresponding to a level of an image signal of a first image period in said image signal and also an enable signal which is in a high level during a period of an image signal of a second image period in said image signal, said inspection means being supplied with said image signal, control signal and enable signal whereby said inspection means is driven during a period where said enable signal is in a high level to conduct said inspection of said object based upon said image signal of the second image period.

2. An object inspection system as claimed in claim 1, in which said last-mentioned means includes a first one-shot timer and a second one-shot timer, said first one-shot timer receiving said position detection signal and producing a strobe signal which is at high level during the first image period of said image signal, and said second one-shot timer receiving an output from said first one-shot timer and producing an enable signal which is at high level during the second image period of said image signal.

3. An object inspection system as claimed in claim 1, in which said last-mentioned means includes a means for smoothing said image signal and means for holding a peak value of an output from said smoothing means.

4. An object inspection system as claimed in any one of claims 2 or 3, in which said holding means includes a gate means which is supplied with the strobe signal to make said holding means operative during a period in which said strobe signal is at a high level.

5. An object inspection system as claimed in claim 4, in which said holding means includes a reset means which receives the position detection signal to reset said holding means at a beginning of the first image period of said image signal.

* * * * *